United States Patent [19]

Halpin-Dohnalek et al.

[11] Patent Number: 5,902,578
[45] Date of Patent: May 11, 1999

[54] METHOD AND FORMULA FOR THE PREVENTION OF DIARRHEA

[75] Inventors: Margaret Ione Halpin-Dohnalek, Worthington; Milo Duane Hilty, Lewis Center; Douglas Gene Bynum, Columbus, all of Ohio

[73] Assignee: Abbott Laboratories, Abbott Park, Ill.

[21] Appl. No.: 08/621,384

[22] Filed: Mar. 25, 1996

[51] Int. Cl.$^6$ .................................................. C12N 1/20
[52] U.S. Cl. ...................... 424/93.3; 424/93.4; 424/93.45
[58] Field of Search ............................... 424/93.4, 93.45, 424/93.3

[56] References Cited

U.S. PATENT DOCUMENTS

| | | | |
|---|---|---|---|
| 4,518,696 | 5/1985 | Gehrman et al. | 435/253 |
| 4,689,226 | 8/1987 | Nurmi et al. | 424/93 |
| 4,839,281 | 6/1989 | Gorbach et al. | 435/34 |
| 4,946,791 | 8/1990 | Manfredi et al. | 435/252.9 |
| 5,021,245 | 6/1991 | Borschel et al. | 426/2 |
| 5,032,399 | 7/1991 | Gorbach et al. | 424/93 |
| 5,190,755 | 3/1993 | Molin et al. | 424/93 J |
| 5,234,702 | 8/1993 | Katz et al. | 426/72 |
| 5,439,678 | 8/1995 | Dobrogosz et al. | 424/93.45 |
| 5,492,899 | 2/1996 | Masor et al. | 514/47 |
| 5,494,664 | 2/1996 | Brassart et al. | 424/93.3 |

FOREIGN PATENT DOCUMENTS

| | | |
|---|---|---|
| 90200426 | 2/1990 | European Pat. Off. . |
| 90312757 | 11/1990 | European Pat. Off. . |
| 92810516 | 7/1992 | European Pat. Off. . |
| 92830653 | 12/1992 | European Pat. Off. . |
| 95200528 | 3/1995 | European Pat. Off. . |
| 62-201823 | 9/1987 | Japan . |
| 01083025 | 3/1989 | Japan . |
| PCT/US91/02445 | 4/1991 | WIPO . |
| WO 91 09608 | 7/1991 | WIPO . |
| WO 97 16198 | 5/1997 | WIPO . |
| WO 97 22352 | 6/1997 | WIPO . |
| WO 97 22353 | 6/1997 | WIPO . |

OTHER PUBLICATIONS

Meeting of the American Society for Clinical Nutrition, Inc., Clinical Division of the American Institute of Nutrition, Baltimore, Maryland, USA, Apr. 30–May 1, 1992. Clin Res 40 (2) 1992, 629A, XP002035131, Heimburger, D.C., et al., "Diarrhea with Enteral Feeding A Randomized Controlled Trial of Prophylactic Lactobacillus Administration".

Database Biosis Biosciences Information Service, Philadelphia, PA, USA, Girola M., et al., "Efficacy of Probiotic Preparation with Living, Freeze–Dried Lactic Acid Bacteria and Yeast on Child Diarrhea" XP002035135, Archivio Di Medicina Interna 47 (2–3), 1995, pp. 61–72.

Joint Meeting of the American Pediatric Society and the Society for Pediatric Research, Washington, D.C., USA, May 6–10, 1996. Pediatric Research 39 (4 Part 2) 1996, 184A, XP002035133, Puiz–Palacios, G., et al., "Tolerance and Fecal Colonization with *Lactobacillus reuteri* in Children Fed a Beverage with a Mixture of Lactobacillus spp."

Joint Meeting of the American Pediatric Society and the Society for Pediatric Research, Washington, D.C., USA, May 6–10, 1996, Pediatric Research 39 (4 Part 2), 1996. 184A, XP002035134, Ruiz–Palacios, G., et al., "Feeding of a Probiotic for the Prevention of Community–Acquired Diarrhea in Young Mexican Children".

Beck, et al. "Beneficial Effects of Administration of *Lactobacillus Acidophilus* in Diarrheal and Other Intestinal Disorders", Medical Research Institute of Michael Reese Hospital, Chicago, Illinois, pp. 522–530.

Elmer, et al. "Biotherapeutic Agents A Neglected Modality for the Treatment and Prevention of Selected Intestinal and Vaginal Infections", *JAMA*, 275: 870–876, (1996).

Wolf, et al. "Safety and Tolerance of *Lactobacillus reuteri* in Healthy Adult Male Subjects", Microbial Ecology In Health and Disease, 8: 41–50, (1995).

Ragout, et al. "Effect of environmental pH on the fermentation balance of *Lactobacillus reuteri*" Journal of Applied Bacteriology, 77: 388–391, (1994).

Boudraa, et al. "Effect of Fermented Infant Formula on Incidence of Diarrhea at Early Weaning", Journal of Pediatric Gastroenterological Nutrition, 19: 339, (1994).

Saavedra, et al. "Feeding of *Bifidobacterium bifidum* and *Streptococcus thermophilus* to infants in hospital for prevention of diarrhoea and shedding of rotavirus", The Lancet, 344: 1046–1049, (1994).

Millar, et al. "Enteral feeding of premature infants with *Lactobacillus GG*", Archives of Disease in Childhood, 69: 483–487, (1993).

(List continued on next page.)

*Primary Examiner*—Jean C. Witz
*Attorney, Agent, or Firm*—Thomas D. Brainard; J. Michael Dixon

[57] ABSTRACT

A novel method for the prevention of infectious diarrhea or diarrhea caused by antibiotic therapy is disclosed. The method comprises the steps of 1) mixing a powder comprising viable cultures of the probiotic organisms *Lactobacillus reuteri, Lactobacillus acidophilus* and *Bifidobacierium infantis* with a liquid; and 2) enterally administering the mixture to a mammal or a human. In a preferred embodiment at least $10^6$ CFU (colony forming units) of each probiotic organism is consumed per day. The invention also relates to pills or capsules containing the probiotic system (*Lactobacillus reuteri, Lactobacillus acidophilus* and *Bifidobacterium infantis*) in a freeze dried or lyophilized form. The invention also relates to a novel powdered nutritional formula for the prevention of diarrhea that comprises protein, fat, carbohydrates and the microorganisms *Lactobacillus reuteri, Lactobacillus acidophilis* and *Bifidobacterium infantis*. In a preferred embodiment the powdered nutritional formula is a nutritionally complete infant formula. A large clinical study has shown that the probiotic system according to the invention when provided in a non-fermented form is efficacious in the prevention of diarrhea. Also disclosed is a method for manufacturing the formula of the invention.

12 Claims, No Drawings

OTHER PUBLICATIONS

Johansson, et al. "Administration of Different Lactobacillus Strains in Fermented Oatmeal Soup: In Vivo Colonization of Human Intestinal Mucosa and Effect on the Indigenous Flora", Applied and Environmental Microbiology, 59: 15–20, (1993).

Kaila, et al. "Enhancement of the Circulating Antibody Secreting Cell Response in Human Diarrhea by a Human Lactobacillus Strain", Pediatric Research, 32: 141–144, (1992).

Perdigón, et al. "Immunoadjuvant activity of oral *Lactobacillus casei:* influence of dose on the secretory immune response and protective capacity in intestinal infections", Jour. of Dairy Research, 58: 485–496, (1991).

Brunser, et al. "Effect of an Acidified Milk on Diarrhoea and the Carrier State in Infants of Low Socio–Economic Stratum", Acta Pædiatr Scand, 78: 259–264, (1989).

Oksanen, et al. "Prevention of Travellers' Diarrhoea by *Lactobacillus GG"*, Annals of Medicine, 22: 53–56, (1990).

Gonzalez, et al. "Prevention of Infantile Diarrhoea by Fermented Milk", Microbiologie–Aliments–Nutrition, 8: 349–354, (1990).

Siitonen, et al. "Effect of *Lactobacillus GG* Yoghurt in Prevention of Antibiotic Associated Diarrhoea", Annals of Medicine, 22: 57–59, (1990).

Perdigón, et al. "Actividad adyuvante de bacterias lácticas: Perspectivas para su uso en vacunas orales", Revista Argentina de Microbiologia, 20: 141–146, (1988).

Vanbelle, et al. "Probiotics in animal nutrition: a review", Arch. Anim. Nutr., 7: 543–567, (1990).

Reuman, et al. "Lack of effect of Lactobacillus on gastrointestinal bacterial colonization in premature infants", Pediatr. Infect. Dis., 5: 663–668, (1986).

Kleeman, et al. "Adherence of Lactobacillus Species to Human Fetal Intestinal Cells", Dairy Science, 65: 2063–2069, (1982).

Klaenhammer, "Microbiological Considerations in Selection and Preparation of Lactobacillus Strains for Use as Dietary Adjuncts", Journal of Dairy Science, 65:1339–1349, (1982).

Kilara, et al. "Use of Lactobacilli in Foods–Unique Benefits", Journal Series of The Pennsylvania Agricultural Experiment Station, pp. 125–138.

Hamdan, et al. "Acidolin: An Antibiotic Produced By *Lactobacillus Acidophilus"* The Journal of Antibiotics, 27: 631–636, (1974).

Hill, et al. "Studies of the Effect of Dietary Lactobacilli on Intestinal and Urinary Amines in Pigs in Relation to Weaning and Post–weaning Diarrhoea", Res. Vet. Sci., 2: 320–326, (1970).

Pearce, et al. "Controlled trial of orally administered lactobacilli in acute infantile diarrhea", Brief clinical and laboratory observations, 84: 261–262.

Fuller, "Probiotics in Man and Animals", Journal of Applied Bacteriology, 66: 365–378, (1989).

Havenaar, et al. "Selections of Strains for Probiotic Use", Huis In't Veld JHJ.

Fuller, "In Scientific Basis of the Probiotic Use", Chapman and Hall.

Gilliland, "Health and Nutritional Benefits from Lactic Acid Bacteria", Micro Rev., 87: 175–188, (1990).

Gorbach, "Lactic Acid Bacteria and Human Health", Annals of Medicine, 22: 37–41, (1990).

Axelsson, "Production of a Broad Spectrum Antimicrobial Substance by *Lactobacillus reuteri"*, Microbial Ecology in Health and Disease 2, pp. 131–136, (1989).

Chung, et al. "In Vitro Studies on Reuterin Synthesis by *Lactobacillus reuteri"*, Microbial Ecology in Health and Disease, 2: 137–144, (1989).

Silva, et al. "Antimicrobial substance from a human lactobacillus stain", Antimicrobe Agents Chemother, 31: 1231–1233, (1987).

METHOD AND FORMULA FOR THE PREVENTION OF DIARRHEA

TECHNICAL FIELD

The present invention relates generally to a method of preventing diarrhea associated with infectious agents such as rotavirus, or diarrhea associated with antibiotic therapies. More specifically, this invention relates to a powdered infant nutritional that contains the probiotic organisms *Lactobacillus reuteri*, *Lactobacillus acidophillus* and *Bifidobacterium infantis*. Administration of at least $10^6$ CFU of each probiotic organism in a 24 hour period has been shown to be effective in the prevention of diarrhea.

BACKGROUND ART

Diarrhea is one of the most common health problems in the world, and even in developed countries is one of the most common infectious diseases. Diarrhea is also one of the most common health problems during childhood. While it has been suggested to administer fermented milk products in the treatment of diarrhea (for example rotavirus associated diarrhea), the medical community continues to seek improved methods or products which would be useful in the prevention of the disease.

In recent years, rotavirus and other enteric viruses have been identified as a major cause of acute diarrhea in infants and young children attending daycare centers. There is an acute need, both domestically and in third world countries, for products and methods that would be effective in preventing infectious diarrhea and diarrhea associated with antibiotic therapy.

Probiotics are a class of microorganisms that are defined as live microbial organisms that beneficially affect the animal and human hosts. The beneficial effects include improvement of the microbial balance of the intestinal microflora or by improving the properties of the indigenous microflora. A better understanding of probiotics in man and animals can be found in the following publications. Fuller R: Probiotics in Man and Animals, *J Appl. Bacteriol* 1989;66:365–365–378 and Havenaar R, Brink B, Huis In't Veld JHJ: Selection of Strains for Probiotic Use. In Scientific Basis of the Probiotic Use, ed. R. Fuller, Chapman and Hall, London UK, 1992.

The known benefits of enteral administration of probiotic microorganisms include enhanced host defense to disease, improving colonization resistance of the harmful microflora and numerous other areas of health promotion. Probiotics have been suggested to play an important role in the formation or establishment of a well-balanced, indigenous, intestinal microflora in newborn children or adults receiving high doses of antibiotics.

Lactic acid bacteria and specific strains of Lactobacillus have been widely recommended for use as probiotics. See, for example, Gilliland SE: Health and Nutritional Benefits from Lactic Acid Bacteria. *Micro Rev.* 1990;87;175–188 and Gorbach SL: Lactic Acid Bacteria and Human Health. Annals of Med. 1990;22–37–41. Species of Streptococci, Enterococcus, and Bifidobacteria have also been suggested as being beneficial. One of the more recently studied probiotics is *Lactobacillus reuteri*. This ubiquitous microorganism resides in the gastrointestinal tract of humans and animals and produces a potent, broad spectrum antimicrobial substance called reuterin. The inhibition of growth of Escherichia, Salmonella, Shigella, Listeria, Campylobacter, Clostridium and species of Staphylococcus by reuterin has been reported. See for example, Axeisson L T, et al (1989), Production of a Broad Spectrum Antimicrobial Substance by *Lactobacillus reuteri*, Microbial Ecology in Health and Disease 2, 131–136.

Of the intestinal lactic acid bacteria (LAB), *L. reuteri* is considered a major species. Due to the inability of microbiologists to distinguish *L. reuteri* from *Lactobacillus fermenyum* (*L. fermetum*) in the past, many researchers believe that a large percentage of LAB classified as *L. fermentum* in older literature, in reality, are strains of *L. reuteri*.

*L. reuteri* is a dominant heterofermentative Lactobacillus species residing in the gastrointestinal tract of healthy humans and most animals. Like other lactobacilli, *L. reuteri* produces acidic metabolic end-products which have considerable antimicrobial activity. It has been recently discovered that metabolism of glycerol by *L. reuteri* can result in excretion of a metabolic intermediate, 3-hydroxpropionaldehyde, or reuterin. See Axelsson, "Production of a Broad Spectrum Antimicrobial Substance by *Lactobacillus reuteri*," *Microbial Ecology in Health and Disease*, 2:131–136, 1989. Reuterin has been shown to have antimicrobial activity against a variety of organisms including Gram-positive and Gram-negative bacteria, yeast, molds and protozoa. See Chung, et al., "In Vitro Studies on Reuterin Synthesis by *Lactobacillus reuteri*," *Microbial Ecology in Health and Disease*, 2:137–144, 1989. It is suspected that the antimicrobial activity of reuterin contributes to the survival of *L. reuteri* within the gastrointestinal ecosystem.

Likewise, *L. acidophilus* is a normal inhabitant of the human gastrointestinal tract and is a Gram-positive rod widely used in the dairy industry. *L. acidophilus* is a homofermentative species, fermenting mainly hexose sugar, yielding predominantly lactic acid (85–95%). The use of *L. acidophilus* predates the 20th century. *Bifidobacterium infantis* is a Gram-positive, strictly anaerobic, fermentative rod. *Bifidobacterium infantis* is the predominant form of Bifidobacterium in breast fed infant feces.

Cultures of these organisms are commercially available and are usually supplied as powders. The cultures are alive but in a dormant state which is achieved by a process known as lyophilization (freeze-drying). BioGaia Biologics, Inc. of Raleigh, N.C. promotes and markets a cultured sweet milk and a fermented milk known as BRA milk™. The cultured sweet milk is made by adding to 1% pasteurized and vitaminized low fat milk a *Lactobacillus reuteri*, *Bifidobacterium infantis*, *Lactobacillus acidophilus* culture mixture just before filling cartons. The fermented BRA milk is similar to the cultured sweet milk except that the organisms are allowed to ferment the milk.

The feeding of Bifidobacterium bifidumand *Streptococcus thermophilus* to infants in hospitals is reported by Savedra, J. et al. in *The Lancet*, Vol. 344, Oct. 15, 1994. The feeding of these two specific organisms was shown to reduce episodes of diarrhea disease over a control (no organisms). 6.9% of the *B. bifidum* and *S. thermophilus* fed infants experienced diarrhea, while 31% of the control group experienced diarrhoeal disease.

U.S. Pat. No. 5,021,245 relates to an infant formula containing a soy polysaccharide fiber source. More specifically, this patent is directed to an infant formula used for the treatment of infantile colic. All of the data and teachings of U.S. Pat. No. 5,021,245 are incorporated herein by reference.

U.S. Pat. No. 5,234,702 relates to a powdered nutritional product which uses a specific antioxidant system to prevent the degradation of the lipid fraction. More specifically, this patent discloses an antioxidant system made up of ascorbyl palmitate, beta carotene and/or mixed tocopherols, and citrate. All of the data and teachings of U.S. Pat. No. 5,234,702 are incorporated herein by reference.

U.S. Pat. No. 5,492,899 discloses an improved enteral nutritional formula containing ribonucleotide equivalents. This patent suggests that such a formula enhances the immune system and alleviates diarrhea. The teachings and data of U.S. Pat. No. 5,492,899 are incorporated herein by reference.

One major aspect that all of the prior art fails to appreciate is the discovery that fermented dairy products, such as yogurts which contain various probiotic agents, present the consuming individual with numerous byproducts that are associated with the fermentation. One aspect of the present invention is the realization that unfermented administration of the probiotic system will be effective in preventing diarrhea. In this regard, pills or capsules containing the probiotic system according to this invention or direct administration of the probiotic powder to the individual is one embodiment of the present invention. Rehydration of the probiotic powder would occur in the patient's stomach and not allow for the fermentation byproducts to form. Thus, the present invention provides an enterally administerable product containing Lacyobacillus reuteri, Lactobacillus acidophilus and Bifidobacterium infantis in an amount which is effective to inhibit diarrhea associated with infectious agents and antibiotic therapy.

DISCLOSURE OF THE INVENTION

There is disclosed a method for the prevention of infectious diarrhea or diarrhea associated with antibiotic therapy in a human, said method comprising the steps of 1) mixing of a powder containing Lactobacillus reuteri, Lactobacillus acidophilus and Bifidobacterium infantis with a liquid and 2) enterally administering an effective amount of said liquid mixture to said human. More specifically the method should result in the administration of at least $10^6$ CFU of Lactobacillus reuteri, $10^6$ Lactobacillus acidophilus and $10^6$ CFU Bifidobacterium infantis per day.

Also disclosed is a nutritional product in powdered form comprising protein, fat, carbohydrates, minerals, vitamins, trace elements and a probiotic system, said probiotic system comprising Lactobacillus reuteri, Lactobacillus acidophilus and Bifidobacterium infantis. In a specific embodiment the powdered nutritional product contains at least $10^5$ CFU Lactobacillus reuteri per gram, $10^4$ CFU Lactobacillus acidophilus per gram and $10^4$ CFU Bifidobacterium infantis per gram.

The infectious diarrhea to be prevented by the present invention may be caused by any known organism that those skilled in this art would understand to cause infectious diarrhea. Such organisms include, but are not limited to: rotavirus, C. difficle, Salmonella, Shigella, Campylobacter, E. coli, Proteus, Pseudomonas, Clostridium, enteric Adenovirus, Ameoba, Staphylococcus, Ova and intestinal parasites such as Giardia Lamblia. The method and composition of the present invention is also efficacious in preventing diarrhea associated with antibiotic therapies. Those skilled in the art appreciate that antibiotic therapy for the treatment for numerous disorders and diseases results in the destruction of the intestinal microflora. This destruction of the intestinal microflora by the antibiotic results in the proliferation of pathological microorganisms. This effect of antibiotic associated diarrhea is well known in the art and readily appreciated by those skilled in this art.

The method according to this invention can also be accomplished through the administration of a powder per se or in the form of a capsule, pill or tablet which incorporates the proper level and types of probiotics disclosed herein. Also contemplated within the scope of this invention is the administration of the probiotic system in a nutritional product. This nutritional product may be, for example, powdered milk, a commercially available infant formula or powdered nutritional supplements. Thus, one aspect of this invention includes the mixing of the probiotics system with a preformed liquid nutritional product (i.e. milk or commercial infant formula). The present invention also contemplates a powdered nutritional product which may be a complete nutritional product or a nutritional supplement comprising vitamins and minerals in conjunction with the probiotic system of this invention. Thus, this invention includes powdered infant formula containing the three probiotic organisms at levels which would deliver the minimum colony forming units (CFU's) during a typical day of feeding.

More specifically, a powdered infant formula according to this invention would supply about $3.5 \times 10^8$ CFU of the probiotic blend per day. The infant formula would contain about $4 \times 10^6$ CFU of the probiotic blend per gram of formula. If one assumes that about 600 mL of formula is consumed per day, then about $7 \times\ ^7$ CFU of L. reuteri is consumed per day if the formula is fortified at $8 \times 10\ ^5$ CFU of L. reuteri per gram of powdered formula.

Also contemplated in this invention is the use of the probiotic system in a nutritional supplement to prevent diarrhea. For example, Gain® nutritional beverage sold by Abbott Laboratories, is fortified with from 1.75 to $8.75 \times 10^6$ CFU per gram of each organism. If 240 mL of the probiotic supplement is consumed per day, then 1.4 to $7.0 \times 10^8$ CFU of the probiotic system is delivered to the patient per day.

There is further disclosed a method for the prevention of infectious diarrhea or diarrhea caused by antibiotic therapy in a human, said method comprising administering to said human in powdered, tablet, pill or capsule form at least $10^5$ CFU Lactobacillus reuteri, at least $10^4$ CFU Lactobacillus acidophilus and at least $10^4$ CFU Bifidobacterium infantis per day There is also disclosed, a method for the production of a powdered nutritional product containing a probiotic system, said method comprising dry blending a powdered probiotic system comprising Lactobacillus reuteri, Lactobacillus acidophilus and Bifidobacterium infantis with said powdered nutritional product.

One important realization that distinguishes this invention from the prior art is that the inclusion of a viable probiotic into a liquid nutritional product substantially prior to consumption will result in a fermented product. Thus, it is important that the probiotic system not be allowed to actively or substantially ferment the liquid product prior to ingestion by a human.

Those skilled in this area of technology will appreciate that for the method of the present invention, to accomplish the prevention of diarrhea, host specific microorganisms should be used.

DETAILED DESCRIPTION OF THE INVENTION

A clinical study was designed to investigate the ability of enteral administration of the probiotic system of this invention (Lactobacillus reuteri, Lactobacillus acidophilus and Bifidobacterium infantis) to prevent infectious diarrhea and diarrhea associated with antibiotic therapy. The study was conducted by adding flavor packets containing the probiotic system of the invention to a base milk just prior to consumption. Thus, the organisms did not have the opportunity to ferment the milk. This feature of administration of the probiotic system in an essentially non-cultured and non-fermented environment is an aspect of the prevention of diarrhea. Example I sets forth the manufacture of the probiotic containing packets and Example II describes the clinical study. The invention will be better understood in view of the following examples, which are illustrative only and should not be construed as limiting the invention.

EXAMPLE I

Manufacture of Probiotic System

The Bifidobacterium infantisused in this experiment is a human isolate and has been deposited with the American Type Culture Center—No. 27920. The *Lactobacillus reuteri* is also a human isolate and is described in U.S. Pat. No. 5,439,678. The *Lactobacillus acidophilus* used herein is a Gram-positive rod well known in the dairy industry. Each organism was grown separately in appropriate media and under conditions which favored viability. The fermentation patterns for each organism are known in the art and have been described previously. For Lactobacillus for example, see Silva M, et al: Antimicrobial substance from a human lactobacillus stain. Antimicrobe Agents Chemother 31:1231–1233, 1987. For cultivating strains of *L. reuteri*, U.S. Pat. No. 5,439,678 should be reviewed. All of the data and teachings of U.S. Pat. No. 5,439,678 are incorporated herein by reference. After fermentation and isolation using techniques known in the industry, the organisms were combined along with a carrier/cryoprotectant (whey protein concentrate) and freeze dried. Other carriers/cryoprotectants such as lactose or maltodextrin can be used. The cultures were combined using dry blending techniques and the resulting inventive culture mixture had the following concentrations:

*Lactobacillus reuteri* at about $5 \times 10^{10}$ CFU/g.

*Lactobacillis acidophilus* at about $5 \times 10^{10}$ CFU/g.

Bifidobacterium infatis at about $6–7 \times 10^{10}$ CFU/g.

This three part culture was manufactured and supplied by BioGala Biologics, Inc., Raleigh, N.C. and is commercially available from BioGaia Biologics.

The flavor packets for the clinical study, including a control (no probiotic system), were manufactured by dry blending the inventive culture mixture described above with sucrose and cocoa powder for the chocolate flavor pouch/packet or sucrose, dextrose and vanilla flavor for the vanilla pouch/packet using a 1.5 cubic foot V-blender to accomplish the blending. The control pouches did not contain the inventive culture mixture.

The packets were 3"×3" foil pouches containing 2.5 g. of the flavor system with or without the inventive probiotic system. Each clinical product was dry blended separately, and the preparations were stored under refrigeration until the required number of pouches had been filled and sealed, and labeled with clinical labels. The control pouches contained no detectable *Lactobacillus reuteri* or *Bifidobacterium infantis*. Completed pouches were stored refrigerated until being shipped to the clinical site in Mexico City. The flavor packets were kept refrigerated until distributed to the children's homes on a weekly basis.

The chocolate flavor packet containing the probiotic system of the present invention had $1.6 \times 10^7$ CFU *L. reuteri* per g; $1.9 \times 10^7$ CFU *L. acidophilus* per g; and $2.3 \times 10^7$ CFU *B. itfantis* per g in the 2.5 g flavor packet. For the vanilla flavor packets manufactured with the probiotic system according to this invention, the cultures were present at $6.35 \times 10^6$ CFU per g for *L. reuteri*; at $2.2 \times 10^7$ CFU per g for *L. acidophihus*; and $1.5 \times 10^7$ CFU per g for *B. infantis*. The probiotic group consumed approximately $1 \times 10^7$ to $4 \times 10^7$ CFU *L. reuteri* per mL in each 4-oz serving, or $10 \times 10^9$ to $5 \times 10^9$ CFU of *L. reuteri* per day. The total daily dose of all three cultures in the probiotic blend for children consuming the probiotic Study Feeding was approximately $2.5 \times 10^8$ CFU per mL or $3.0 \times 10^{10}$ CFU per day.

EXAMPLE II

Clinical Study

The following clinical study was conducted under protocol number CP-AG08 and the results were reported in a final report issued Sep. 29, 1995.

258 children living in Mexico City, Mexico were invited to join the clinical study. These children were 12 to 36 months of age and had a history of ingesting cow's milk or cow's-milk-based infant formula as part of their daily diet. Children were excluded that had a history of allergy to cow's milk; were being breast fed; had clinical evidence of chronic gastroenteritis; had clinical evidence of chronic or severe renal, liver or gastrointestinal tract function; were on immunosuppressive therapy; had taken an investigational drug within 30 days prior to enrollment or were involved in another clinical study.

Parents or legal guardians of the study subjects signed an informed consent approved by the Institutional Review Board for the Department of Infectious Diseases at the National Institute of Nutrition in Mexico City, Mexico. The investigators, staff, and parents responsible for care of the children remained blinded to the type of feedings administered to the children. The parents or legal guardians also agreed to provide the Study Feeding (base milk plus flavor packet) twice daily during the 16 week study and agreed not to give yogurt or other cultured products during the clinical trial.

The children were randomized to receive one of two Study Feedings (control vs. experimental) in a blinded, parallel, 16 week feeding trail. Randomization was stratified by age and gender. The study consisted of an entry baseline evaluation phase and the 16 week feeding phase. All children were placed under active surveillance for diarrhea during the study. At least seven days prior to beginning the trial (baseline evaluation phase) each child consumed the base study milk which was whole milk packaged in single-serving Tetra Paks (240 ml) obtained from a commercial manufacturer in Mexico City.

Parents were instructed on how to complete the monthly visit evaluation forms, how to collect fecal samples, how to mix the base study milk with the flavor packets and what to do when their child developed diarrhea.

The Study Feeding Phase began the first day the base study milk plus clinically labeled flavor packet was given and continued through day 112 or until the study ended or the child exited the study. Parents received clinically labeled color coded chocolate and vanilla flavor packets each week to mix with the base milk. Each flavor packet was mixed with 120 mL of base milk. Daily intake was recorded by the parents on worksheets.

Parents were allowed to store the packets unopened at room temperature during the week. 120 mL of base milk plus one flavor pouch was fed in the morning and another 120 mL of base milk plus flavor pouch was fed in the evening. Once mixed, the Study Feeding was consumed; any beverage not consumed within 5 hrs. was discarded. The amount of beverage consumed was recorded for each feeding. Stool samples were taken and stool characteristics were evaluated at entry and on Study Days 28, 56, 84 and 112. Diaries were used to record the child's stool patterns and tolerance.

Antibiotic use was assessed and recorded weekly by study social workers during interviews with parents. Information of the drug name, dates of use and reason for use were also recorded. The children were actively observed for diarrhea. Diarrhea was defined as an acute change in stool pattern with three or more watery/liquid stools in a 24 hr period or two or more stools than normal which were looser than normal consistency or if a child had a watery or pasty stool with blood, diarrhea was considered present.

Parents contacted the investigators when a child passed the first diarrhea stool. Records regarding number of stools and consistency were taken. Stool samples were also taken. The Study Feeding was continued during the diarrhea episode unless it interfered with the medical management of the illness. Diarrhea was tracked until the stool pattern (number and consistency) returned to normal for the child.

Also important was antibiotic use associated with any diarrhea episodes. Antibiotic associated diarrhea was defined as an episode of diarrhea that developed during antibiotic therapy or within 14 days after an antibiotic was stopped for which there was no enteric pathogens other than *C. difficile* (as detected by presence of *C. difficile* toxin) identified in the stool specimen collected during the episode.

Diarrhea stool samples were collected for evaluation of rotavirus and enteric adenovirus; for enteric pathogens; for *Clostridium difficile* toxin; and, selected parasites.

Statistical Methods

For continuous outcomes (percent watery stools, percent watery/loose stools, mean rank stool consistency, average number of stools per day, percent feedings, average number of feedings per day, average daily intake which were measured at several visits), repeated measures analysis of variance was employed. Values at Day 28, Day 56, Day 84 and Day 112 were responses.

The number of cases of diarrhea was analyzed by the marginal approach to multivariate survival analysis. Time to the first episode of diarrhea was analyzed by the Cox regression with the robust estimator of the variance. A multivariate Cox regression was performed comparing the number of episodes of diarrhea in the feeding groups. This analysis counts all episodes of diarrhea, including repeated episodes. The marginal approach of Lin, Wei and Weisfield was used to analyze the data. The generalized estimating equations technique is used due to the fact that some individuals have repeat episodes. We assume that the effect of the probiotic feeding is the same for first and for repeat episodes. A Cox regression analysis was also performed for first episodes, ignoring repeat episodes. Analysis was also done for first episodes and for all episodes that occurred ≧8 days of study feeding.

RESULTS

Study Entrance Data

Two hundred fifty eight children received randomization numbers and signed informed consent to enter the study, 129 subjects in each group. The entry age ranged from 12.2 months to 36.9 months for the control group (median=23.2 months) and from 12.0 to 36.6 months for the probiotic group (median=24.0 months). The mean age of children randomized was similar across both groups. For the 243 children that entered the study and received the Study Feeding, the mean age in the control group was 24.0±0.7 months, and 24.1±0.6 months for the probiotic group. No statistically significant differences were seen in entry data for sex, age, and prior serious illness. All 243 subjects receiving the Study Feeding were placed under diarrhea surveillance (120 children in the control group and 123 children in the probiotic group).

Study Feeding Phase

Mean days on Study Feeding were 94.8±2.5 days for the control group and 95.9±2.6 days for subjects receiving the probiotic feeding. Median days on the study (111.0 days), and number of days on Study Feeding for the 75th percentile (111.0 days) and 25th percentile (97.0 days) were the same for both groups. Length of feeding for subjects who successfully completed the study ranged from 88 to 120 days. Study feeding for subjects in the control group ranged from 88 to 120 days, and from 97 to 111 days for the probiotic group.

The Study Feeding consisted of two 4-oz (about 120mL) feedings of whole milk (base milk) with added flavor packet, constituting only a minor portion of the daily caloric intake for the child. Subjects were allowed to consume regular milk in addition to the Study Feeding, and ice cream, solid foods, cheeses, juices and/or cereals were also permitted. The only restrictions were on the consumption of yogurts and other cultured products, and on the consumption of other probiotic-containing products.

Study Feeding Intake

Average daily intake was consistent for both groups (control vs. experimental) among the children consuming the Study Feeding. Intake was noted daily for all children participating in the study and total daily intake was recorded on study records.

Episodes of Diarrhea

Emphasis was given to the analysis of diarrhea episodes on Study Day 8 or later, thus subjects on the Study Feeding less than eight days were excluded. Of the 243 subjects who received the Study Feeding, four exited the study within the first seven days, all in the probiotic group. This gave 239 subjects with diarrhea surveillance beyond Study Day 7, with 120 subjects in the control group and 119 in the probiotic group.

There was a statistically significant difference between reported episodes of diarrhea occurring ≧8 days on Study Feeding for the two groups (Table 1). Among the 120 subjects in the control group with ≧8 days on Study Feeding, there were 51 reported episodes of diarrhea (0.425 episodes per subject). For the probiotic group, 33 episodes of diarrhea were reported (0.277 episodes per child) after at least 7 days on Study Feeding. Statistical evaluation by the marginal Cox Regression Analysis with robust, GEE estimate of the variance for the number of diarrhea episodes in the feeding groups was p=0.0385. The relative risk of diarrhea for a child receiving the probiotic feeding relative to the control feeding gives a point estimate of 0.592.

TABLE I

Incidence of Diarrhea Episodes As
Reported By Frequency By Group ≧ 8 Days on Study Feeding

|  | Control | Probiotic | Total |
|---|---|---|---|
| No Episode | 77 (64.2%) | 90 (75.6%) | 167 |
| One Episode | 37 (30.8%) | 25 (21.0%) | 62 |
| Two Episodes | 5 (4.2%) | 4 (3.4%) | 9 |
| Three Episodes | 0 | 0 | 0 |
| Four Episodes | 1 (0.8%) | 0 | 1 |
| TOTAL | 120 | 119 | 239 | p = 0.0385

Diarrhea Stool Samples

There were a total of 106 episodes of diarrhea tracked during the clinical trial. Of these, 84 episodes occurred ≧8 days on Study Feeding. Rotavirus ELISA was positive in a total of 12 stool samples and for nine diarrhea samples collected for subjects with an episode ≧8 days on Study Feeding (Table II).

TABLE II

Incidence of Rotavirus (RV) Positive Diarrhea Stool Samples
For Episodes and ≧8 Days After Study Feeding, By Group

|  | Control | Probiotic |
|---|---|---|
| No. RV + Stool Samples | 9 | 3 |
| No. RV + Stool Samples ≧8 Days on Study Feeding for Subjects at Risk | 7/107 | 2/107 |

Antibiotic Associated Diarrhea

Six episodes of antibiotic-associated diarrhea that developed during antibiotic therapy or within 14 days after an antibiotic was stopped, and for which no enteric pathogen was identified in a diarrhea stool, were identified, all in the control group (Table III).

TABLE III

Incidence of Antibiotic Associated Diarrhea For
Episodes ≧8 Days After
Study Feeding, By Group for Subjects at Risk

|  | Control | Probiotic |
|---|---|---|
| Antibiotic Associated Diarrhea ≧8 Days on Study Feeding for Subjects at Risk | 6/120 | 0/119 |

Severity and Duration

There were no statistically significant differences in the severity scores of diarrhea for episodes that occurred after ≧8 days on Study Feeding.

Antibiotic Use

No statistically significant differences were seen in frequency of antibiotic use reported between the two feeding groups. Over 70% of the subjects in both groups took an antibiotic at least once during the Study Feeding Phase.

Conclusions

The Study Feeding, whole milk with a flavor packet added, was well received by the children participating in the study. Data indicate that use of the flavor packets containing the probiotic system according to this invention and added to milk at point of consumption, was effective in preventing the onset of infectious diarrhea or diarrhea caused by antibiotic therapy. Through the work of the inventors it has been shown that the probiotic system of the present invention is efficacious and has been determined to be safe. This large clinical trial was designed to evaluate the disclosed and claimed probiotic system to determine if it is effective in reducing the incidence and severity of infectious and antibiotic diarrhea. This study has demonstrated that children consuming the inventive probiotic-containing beverage were at a reduced risk of diarrhea compared to children receiving the control beverage. Differences were statistically significant and support the efficacy of the present invention in reducing the incidence of diarrhea in children when taken as part of the daily diet.

INDUSTRIAL APPLICABILITY

The results from the clinical study demonstrate that method and formula of this invention is effective in the prevention of diarrhea. The medical community is constantly searching for methods and products that will benefit the infant and the adult. The present invention can clearly fill that need. In addition, the products useful in the method claimed herein utilizes conventional equipment and may be readily accomplished.

While the methods and products herein described constitute a preferred embodiment of this invention; it is to be understood that the invention is not limited to the precise method or formulation and that changes may be made therein without departing from the scope of the invention which is defined in the appended claims.

What is claimed is:

1. A method for reducing the incidence of infectious diarrhea or diarrhea caused by antibiotic therapy in a human, said method comprising the steps of 1) mixing of a powder containing viable *Lactobacillus reuteri, Lactobacillus acidophilus* and *Bifidobacterium infantis* with a liquid and 2) enterally administering an effective amount of said liquid mixture to said human prior to the formation of fermentation by-products.

2. A method according to claim 1 wherein infectious diarrhea is caused by an organism selected from the group consisting of rotavirus, *C. difficile*, Salmonella, Shigella, Campylobacter, *E. coli*, Proteus, Pseudomonas, Clostridium, enteric Adenovirus, Ameoba, Staphylococcus, Ova and *Giardia lamblia*.

3. A method according to claim 1 wherein said powder additionally comprises protein, fat, carbohydrates, fiber, vitamins, minerals and trace elements.

4. A method according to claim 1 wherein said powder contains from $10^5$ to $10^{10}$ CFU of *Lactobacillus reuteri* per gm., $10^5$ to $10^{10}$ CFU of *Lactobacillus acidophilus* per gm. and $10^5$ to $10^{10}$ CFU of *Bifidobacterium infantis* per gm.

5. A method according to claim 1 wherein from $10^6$ to $10^{10}$ CFU of each of said *Lactobacillus reuteri, Lactobacillus acidophilus* and *Bifidobacterium infantis* is enterally administered per day.

6. A nutritional product in powdered form comprising protein, fat, carbohydrates, minerals, vitamins, trace elements and a probiotic system, said probiotic system comprising *Lactobacillus reuteri, Lactobacillus acidophilus* and *Bifidobacterium infantis*.

7. A nutritional product in powdered form according to claim 6 wherein said probiotic system comprises at least $10^5$ CFU *Lactobacillus reuteri* per gm., $10^4$ CFU *Lactobacillus acidophilus* per gm. and $10^4$ CFU *Bifidobacterium infantis* per gm.

8. A nutritional product according to claim 6 wherein said protein, fat and carbohydrates are present in concentrations such that, upon dissolution in a specified quantity of water to make a formula the concentration of said protein being between 10 and 25 grams per liter of formula; said fat being between 20 and 45 grams per liter of formula; and said carbohydrates being between 60 and 110 grams per liter of formula.

9. A nutritional product according to claim 8 wherein said probiotic system is at concentration of at least $10^2$ CFU per liter of formula.

10. A nutritional supplement in the form of a capsule, pill or tablet comprising vitamins and minerals and a probiotic system, said probiotic system comprising *Lactobacillus reuteri, Lactobacillus acidophilus* and *Bifidobacterium infantis.*

11. A method for reducing the incidence of infectious diarrhea or diarrhea caused by antibiotic therapy in a human, said method comprising administering to said human in powdered, tablet, pill or capsule form at least $8 \times 10^5$ CFU *Lactobacillus reuteri*, at least $10^4$ CFU *Lactobacillus acidophilus and at least* $10^4$ CFU *Bifidobacterium infantis per day.*

12. A method for the production of a powdered nutritional product containing a lyophilized probiotic system, said method comprising dry blending a powdered probiotic system comprising *Lactobacillus reuteri, Lactobacillus acidophilus* and *Bifidobacterium infantis* with at least one component selected from sucrose, cocoa powder and vanilla flavor.

\* \* \* \* \*